(12) United States Patent
Ouchi

(10) Patent No.: US 8,735,823 B2
(45) Date of Patent: May 27, 2014

(54) TERAHERTZ-WAVE ELEMENT, TERAHERTZ-WAVE DETECTING DEVICE, TERAHERTZ TIME-DOMAIN SPECTROSCOPY SYSTEM, AND TOMOGRAPHY APPARATUS

(75) Inventor: Toshihiko Ouchi, Machida (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/979,624

(22) PCT Filed: Jan. 10, 2012

(86) PCT No.: PCT/JP2012/050660
§ 371 (c)(1),
(2), (4) Date: Jul. 12, 2013

(87) PCT Pub. No.: WO2012/096398
PCT Pub. Date: Jul. 19, 2012

(65) Prior Publication Data
US 2013/0284929 A1 Oct. 31, 2013

(30) Foreign Application Priority Data

Jan. 14, 2011 (JP) .................. 2011-006123
Oct. 19, 2011 (JP) .................. 2011-230004

(51) Int. Cl.
*G01J 5/02* (2006.01)
*G01N 21/35* (2014.01)
*G01J 5/08* (2006.01)
(52) U.S. Cl.
CPC ........ *G01N 21/3586* (2013.01); *G02F 2203/13* (2013.01); *G01J 5/0818* (2013.01)
USPC ................... 250/341.1; 250/338.1

(58) Field of Classification Search
CPC . G01J 5/0818; G01N 21/3586; G02F 1/0126; G02F 1/3511; G02F 1/3515; G02F 1/3517; G02F 1/365; G02F 2203/13
USPC ........................... 250/338.1, 341.1
See application file for complete search history.

(56) References Cited

U.S. PATENT DOCUMENTS 3,644,846 A 2/1972 Bridges et al.
2005/0242287 A1 11/2005 Hakimi

FOREIGN PATENT DOCUMENTS

| EP | 2175308 A1 | 4/2010 |
|---|---|---|
| JP | 5-224250 A | 9/1993 |
| JP | 3388319 B2 | 3/2003 |
| JP | 2010-204488 A | 9/2010 |
| WO | 2007/070575 A2 | 6/2007 |

OTHER PUBLICATIONS

Masahiko Tani, Kazuki Horita, Tetsuya Kinoshita, Christopher T. Que, Kohji Yamamoto, Michael I. Bakunov, Efficient Electro-Optic Sampling Detection of Terahertz Radiation via Cherenkov Phase Matching, Annual Meeting of the Spectroscopical Society of Japan (Extended Abstracts), Nov. 18-20, 2010, Kyoto, Japan, p. 128, Spectroscopical Society of Japan, Tokyo, Japan, 2010.

(Continued)

*Primary Examiner* — Mark R Gaworecki
(74) *Attorney, Agent, or Firm* — Canon USA Inc IP Division

(57) ABSTRACT

A terahertz-wave element includes a waveguide (2, 4, 5) that includes an electro-optic crystal and allows light to propagate therethrough, and a coupling member (7) that causes a terahertz wave to enter the waveguide (2, 4, 5). The propagation state of the light propagating through the waveguide (2, 4, 5) changes as the terahertz wave enters the waveguide (2, 4, 5) via the coupling member (7).

16 Claims, 10 Drawing Sheets

(56) References Cited

OTHER PUBLICATIONS

Masahiko Tani, Kazuki Horita, Tetsuya Kinoshita, Christopher T. Que, Kohji Yamamoto, Michael I. Bakunov, Efficient Electro-Optic Sampling Detection of THz Wave with Cherenkov-Type Phase Matching, 2010, University of Fukui, Fukui, Japan, 2010.

Koji Suizu, Kaoru Koketsu, Takayuki Shibuya, Toshihiro Tsutsui, Takuya Akiba, Kodo Kawase, Extremely Frequency-Widened Terahertz Wave Generation Using Cherenkov-Type Radiation, Optics Express, Apr. 13, 2009, 17(8):6676-6681, The Optical Society, Washington DC, 2009.

LASER LIGHT
TERAHERTZ WAVE

TERAHERTZ-WAVE ELEMENT, TERAHERTZ-WAVE DETECTING DEVICE, TERAHERTZ TIME-DOMAIN SPECTROSCOPY SYSTEM, AND TOMOGRAPHY APPARATUS

TECHNICAL FIELD

The present invention relates to terahertz-wave elements, terahertz-wave detecting devices, terahertz time-domain spectroscopy systems, and tomography apparatuses.

BACKGROUND ART

In recent years, non-destructive sensing techniques using electromagnetic waves in a frequency range between 30 GHz and 30 THz (terahertz waves) have been developed.

As a terahertz-wave detecting method, a method that employs a nonlinear optic crystal is widely used. Typical examples of nonlinear optic crystals include LiNbOx (lithium niobate, referred to as "LN" hereinafter), LiTaOx, NbTaOx, KTP, DAST, ZnTe, and GaSe. For detecting a terahertz wave using a nonlinear crystal, a Pockels effect (which is a kind of a second-order nonlinear phenomenon), which is a first-order electro-optic effect, is used. Specifically, when light is irradiated as probe light onto the same location as a terahertz wave, the polarization state of the probe light changes in accordance with the electric field of the terahertz wave. The amount of change in the polarization state is detected by a polarizing element and a light detector (see PTL 1). In an element that uses such a nonlinear crystal, the wavelength band of the probe light is wide so as to allow for a 0.8-μm band or even a so-called communication wavelength band of 1 μm or greater, thereby advantageously allowing for the use of an inexpensive light source, such as a fiber laser.

In PTL 1, the polarization of the probe light is changed by so-called vertical operation. Since the thickness of the crystal is equivalent to the interaction distance, the sensitivity can be increased with increasing thickness by performing phase-matching. However, in order to achieve phase-matching with a terahertz wave in a wideband, the crystal needs to be reduced in thickness, meaning that the sensitivity and the frequency band are in a trade-off relationship. For improving sensitivity by increasing the interaction distance, there has been a proposal in which the nonlinear crystal is operated horizontally (see NPL 1). In this case, a Cerenkov phase-matching method that utilizes dispersion of the terahertz wave and the probe light within the nonlinear crystal is discussed as a phase-matching method.

There have also been proposals with regard to generating a terahertz wave by a Cerenkov phase-matching method (see PTL 2 and NPL 2).

CITATION LIST

Patent Literature

PTL 1 Japanese Patent No. 03388319
PTL 2 Japanese Patent Laid-Open No. 2010-204488

Non Patent Literature

NPL 1 2010 Annual Meeting of the Spectroscopical Society of Japan, p. 43 (Extended Abstracts, p. 128)
NPL 2 Opt. Express, vol. 17, pp. 6676-6681, 2009

SUMMARY OF INVENTION

Technical Problem

However, in Cerenkov phase-matching discussed in NTL 1, the nonlinear crystal used is an LN crystal having a thickness of 0.5 mm, and the propagation state of the light input as probe light significantly varies depending on how the crystal is coupled to the waveguide. Specifically, the input light often propagates in multiple modes and becomes an aggregate of light rays with multiple group velocities, which is problematic in terms of response velocity. Furthermore, the time that it takes for a terahertz wave coupled via an Si prism to reach the probe light varies in the thickness direction of the LN crystal. For example, assuming that a terahertz wave enters the LN crystal having a thickness of 0.5 mm and a refractive index of 2.2, a time difference of about 4 ps occurs. Therefore, the frequency of a terahertz wave that can be phase-matched is limited.

With regard to detection of a terahertz wave using a high-sensitivity nonlinear optic crystal of a horizontal operation type, the present invention allows for a wider detectable terahertz-wave frequency band by expanding the band that can be phase-matched.

Solution to Problem

A terahertz-wave element according to an aspect of the present invention includes a waveguide that includes an electro-optic crystal and allows light to propagate therethrough; and a coupling member that causes a terahertz wave to enter the waveguide. A propagation state of the light propagating through the waveguide changes as the terahertz wave enters the waveguide via the coupling member.

Advantageous Effects of Invention

A high-sensitivity, wideband terahertz-wave detecting element can be provided.

DESCRIPTION OF EMBODIMENTS

First Embodiment

Figure 1A:
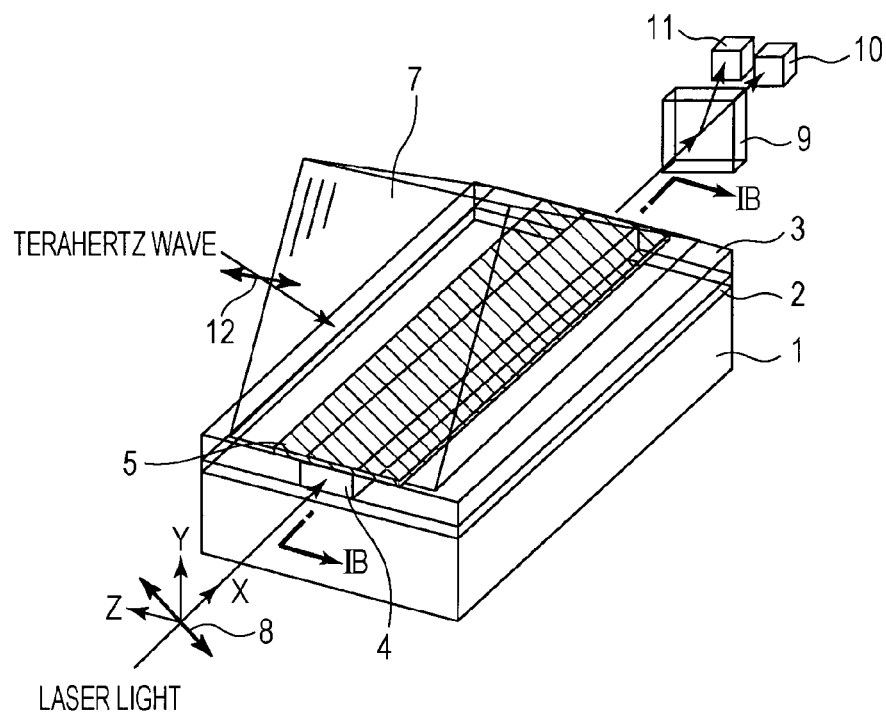
FIGS. 1A and 1B are structural diagrams of a terahertz-wave element according to a first embodiment of the present invention.
Figure 1B:
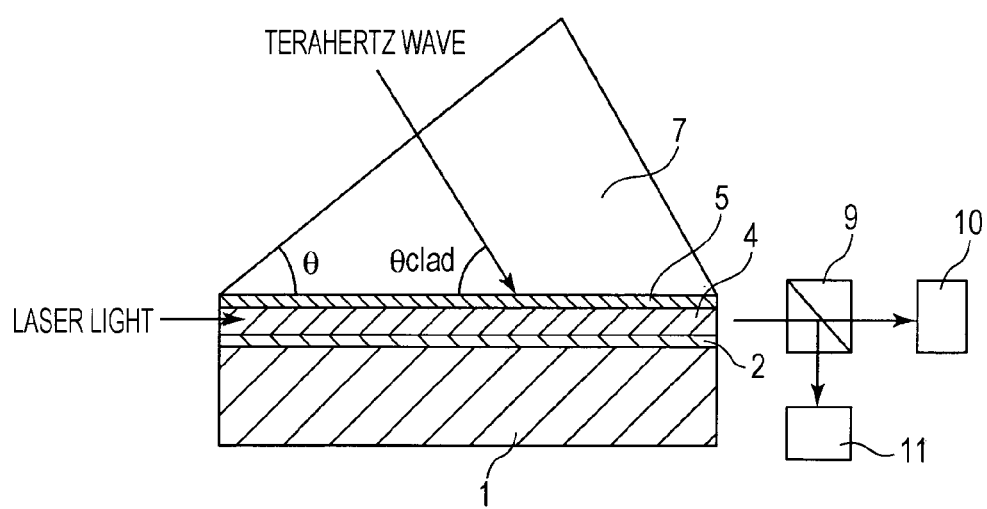

A terahertz-wave element composed of an LN crystal according to a first embodiment of the present invention will now be described with reference to FIGS. 1A and 1B. FIG. 1A is a perspective view, and FIG. 1B is a cross-sectional view taken along line IB-IB in a waveguide section.

An LN substrate 1 is composed of Y-cut lithium niobate, and the LN crystal has an X axis corresponding to a propagating direction of laser light and a Z axis corresponding to a direction orthogonal to the propagating direction (see coordinate axes shown in FIG. 1A). With such a configuration, a change in refractive index effectively occurs due to a first-order electro-optic effect (Pockels effect) by a terahertz wave, denoted by reference numeral 12 in FIG. 1A, entering as an S-polarized wave (i.e., a linearly-polarized wave parallel to the Z axis of the LN crystal in this embodiment). On the LN substrate 1, an adhesive layer 2, a waveguide layer 4 formed of an MgO-doped LN crystal layer, and a low-refractive-index buffer layer 5 form a waveguide that allows input laser light to propagate therethrough by total internal reflection. Specifically, the refractive indices of the adhesive layer 2 and the low-refractive-index buffer layer 5 are set to be lower than that of the waveguide layer 4. The waveguide layer 4 is a core layer serving as a core for the laser light, whereas the adhesive layer 2 and the buffer layer 5 are cladding layers serving as cladding for the laser light. The adhesive layer 2 is required if the waveguide is to be fabricated by bonding the components together, but is not necessarily required if a doped layer is to be formed by diffusion or the like. Even in this case, the function of a waveguide is still achieved since the MgO-doped LN layer has a refractive index that is higher than that of the LN substrate 1. The waveguide can be formed by varying the refractive indices between the waveguide layer 4 and a surrounding region 3 by increasing the refractive index of the waveguide layer 4 by Ti diffusion, or by forming the waveguide layer 4 into a ridge pattern by etching and embedding resin or the like into the surrounding region 3. Alternatively, the surrounding region 3 may be kept in a state of void without embedding anything therein. Although the waveguide structure is also formed in the lateral direction, like the waveguide layer 4, so as to increase the light confinement properties, a slab waveguide in which the region of the waveguide layer 4 extends uniformly in the lateral direction so as to not to have a confinement region, like the surrounding region 3, is also permissible. Alternatively, multiple waveguide layers 4 may be arranged in parallel to each other in the lateral direction so as to increase a terahertz-wave light-receiving region while controlling the light waveguide mode. On the low-refractive-index buffer layer 5, an optical coupling member 7, such as a prism, a diffraction grating, or a photonic crystal, that couples a terahertz wave to be detected to the waveguide from the outside is provided at least above the waveguide. The thickness of the buffer layer 5 is preferably large enough to function as a cladding layer when the laser light propagates through the waveguide layer 4, but small enough that the effect of multiple reflection and loss is negligible when the terahertz wave enters the optical coupling member 7. Regarding the former, in the waveguide in which the waveguide layer 4 as a high-refractive-index layer serves as a core whereas the low-refractive-index layers 2 and 5 serve as cladding, the aforementioned thickness is preferably greater than or equal to a thickness with which the light intensity at an interface between the low-refractive-index buffer layer 5 and the optical coupling member 7 is lower than or equal to $1/e^2$ of the light intensity of a core region. It should be noted that e is the base of natural logarithm. Regarding the latter, the thickness is preferably smaller than or equal to about 1/10 of an equivalent wavelength $\lambda_{eq}$ (THz), in the low-refractive-index buffer layer 5, of an input terahertz wave at the maximum frequency. This is because, in a structural body with a size corresponding to 1/10 of a wavelength, the effects of reflection, dispersion, refraction, and the like on an electromagnetic wave with that wavelength are generally considered to be negligible. It should be noted, however, that terahertz-wave detection using the terahertz-wave element according to the present invention is possible even outside the aforementioned preferred thickness range.

Figure 2:
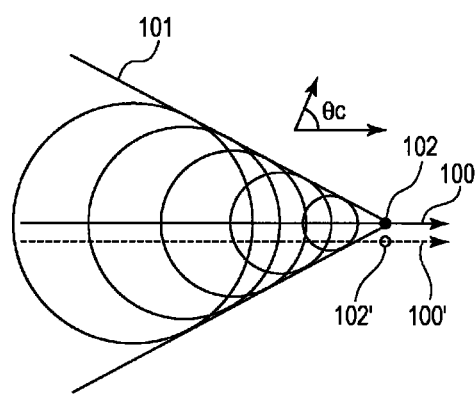
FIG. 2 is a configuration diagram of a tomography apparatus according to the first embodiment of the present invention.

Cerenkov phase-matching will now be described with reference to FIG. 2. This can be easily appreciated on the basis of the concept of electro-optic Cerenkov radiation that generates a terahertz wave from a nonlinear optic crystal. In FIG. 2, when the propagation velocity of laser light 100 serving as an excitation source is higher than the propagation velocity of a generated terahertz wave, a terahertz wave 101 is released in the form of a cone, like a shock wave. In the case of a normal electro-optic crystal bulk body, a radiation angle θc (i.e., an angle θc between the light and the terahertz wave) is determined from the following equation (1), which is the ratio of refractive indices of the light and the terahertz wave within the medium (i.e., nonlinear optic crystal).

$$\cos\theta_c = \frac{v_{THz}}{v_g} = \frac{n_g}{n_{THz}} \quad (1)$$

In this case, vg and ng respectively denote the group velocity and the group refractive index of excitation light relative to the nonlinear optic crystal, and $v_{THz}$ and $n_{THz}$ respectively denote the phase velocity and the refractive index of a terahertz wave relative to the nonlinear optic crystal. For example, there has been a report in NPL 2 (PTL 2) with regard to generating a wideband monochromatic terahertz wave by a difference frequency generation method based on Cerenkov phase-matching by using a slab waveguide having a thickness that is sufficiently smaller than the wavelength of a generated terahertz wave. In this case, ng and $n_{THz}$ are effective refractive indices of the light and the terahertz wave. For example, ng is the group refractive index of the waveguide relative to the light. If a prism for optical coupling exists in the vicinity of the waveguide as in NPL 2 (PTL 2), it is also necessary to consider radiation in view of the refractive index of the prism. Therefore, $n_{THz}$ is an effective refractive index of the terahertz wave determined from the waveguide and the coupling member (prism). If the waveguide is thin, θc can be adjusted by selecting an appropriate material for the prism.

Regarding a reverse process of this generation process, when the wavefront of the terahertz wave is returning, a relationship that is the same as that in the aforementioned equation (1) should be satisfied in order to cause a point of a front 102 of the laser light 100 to constantly interact with the terahertz wave while similarly returning to the laser source. This is called Cerenkov phase-matching that is used when detecting a terahertz wave. In this case, it is important that, for example, an interaction occurs between the terahertz wave and the laser light at the point 102. Therefore, when the propagating area of the laser light reaches a thickness substantially equivalent to the wavelength of the terahertz wave (e.g., a width between 100 and 100'), the interaction point blurs at the wavefront of the interacting terahertz wave due to a time difference between points above and below (102 and 102') the aforementioned propagating area. When such blurring occurs, the terahertz-wave element becomes incapable of responding to a high-speed change, that is, a high frequency, of the terahertz wave. A quantitative description of the thickness will be provided later.

Next, a detection mechanism of a detecting unit will be described. When linearly-polarized laser light tilted at, for example, 45° relative to the Z axis enters the waveguide layer 4 and propagates therethrough along the X axis, as shown in FIG. 1, the polarization state changes due to birefringence of the LN crystal even in a state where a terahertz wave is not input (natural birefringence). The polarization state of the propagated light output from a surface different from the input surface can be checked by performing balance reception using a Wollaston prism 9 and two photodiodes 10 and 11. Regarding the output laser light in this case, a phase difference occurs between a Z-axis component and a Y-axis component of an electric field due to birefringence of the electro-optic crystal, causing the light to propagate as an elliptically polarized wave. The phase difference occurring due to such natural birefringence varies depending on the type of crystal (LN is 3 m crystal), the input polarization direction, and the waveguide length, and a configuration for zero phase difference is also possible. A polarization variation in a state where there are no terahertz signals may be adjusted using a known compensating plate (not shown) so as to cancel offsets. Since a detailed description is provided in PTL 1, the description will be omitted here.

With regard to the interaction occurring when a terahertz wave is input in this embodiment, the interaction is made to occur by utilizing a change in the polarization state of the propagating light owing to a change in the refractive index of the waveguide on the Z axis caused by a first-order electro-optic effect imparted on the electro-optic crystal by a terahertz electromagnetic field. Specifically, the phase difference between the Z-axis component and the Y-axis component of the electric field of the laser light changes due to induced birefringence, causing the ellipticity of the elliptically polarized wave and the direction of the main axis to change.

By detecting the change in the propagation state of the laser light on the basis of differential amplification by using an external polarizing element (such as the Wollaston prism 9) and light detectors (such as the photodiodes 10 and 11), the electric-field amplitude of the terahertz wave can be detected. The differential amplification is not mandatory, and the intensity may be detected with only a single light detector using the Wollaston prism 9 as a polarizer.

Furthermore, although a method for detecting a change in the polarization state of propagating light has been described above, there is also a method for detecting a change imparted on the propagating light by an interaction between a terahertz wave generated by the propagating light and a terahertz wave input from the outside as a change in the oscillation frequency or the light intensity of the propagating light. In that case, light detectors alone are sufficient and the polarizing element is not necessary, and the polarization plane of input light may be parallel to the Z axis.

Although the detecting unit described above is necessary when converting a terahertz-wave signal to an electric signal, the detecting unit is not necessary if the laser light itself is modulated and the modulated light is used at a later stage. This applies to when, for example, the terahertz-wave element according to the present invention is used as a light modulator that uses a terahertz wave.

Figure 3A:
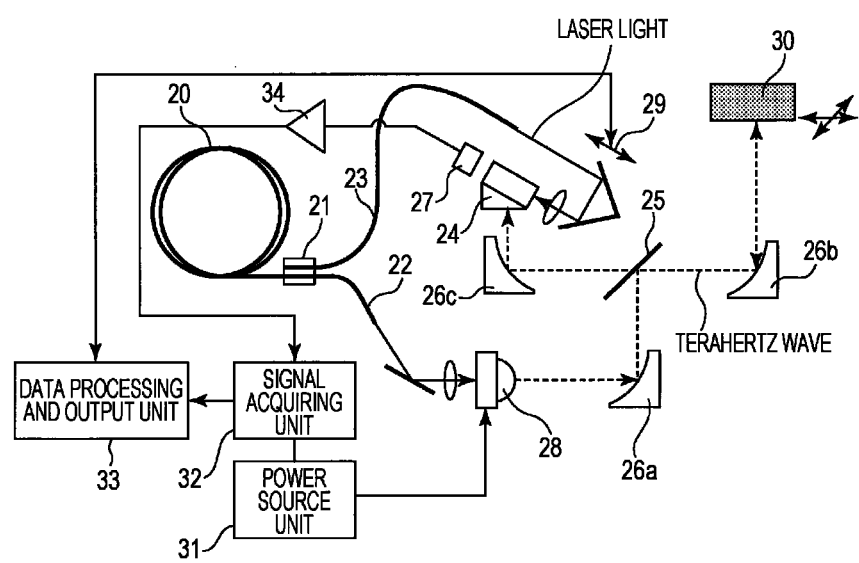
FIGS. 3A and 3B are diagrams for explaining Cerenkov phase-matching.
Figure 3B:
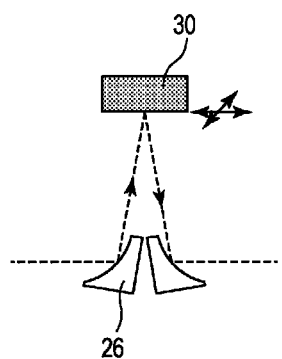

FIGS. 3A and 3B illustrate an example of a tomographic imaging apparatus (tomography apparatus) based on a terahertz time-domain spectroscopy system (THz-TDS) that uses the terahertz-wave element according to this embodiment as a terahertz-wave detecting element.

A femtosecond laser 20 including optical fibers is used as an excitation light source, and an output therefrom is extracted from a fiber 22 and a fiber 23 via a splitter 21. Although the femtosecond laser 20 used normally has a center wavelength of 1.55 μm, a pulse width of 20 fs, and a cyclic frequency of 50 MHz, the wavelength may alternatively be in a 1.06-μm band, and the pulse width and the cyclic frequency are not limited to the aforementioned values.

Furthermore, the fibers 22 and 23 at the output stage may each include a high nonlinear fiber for high-order soliton compression at the final stage or a dispersive fiber that performs prechirping for compensating for dispersion caused by an optical element or the like extending to a terahertz generator and a terahertz detector. These fibers are preferably polarization-maintaining fibers.

The terahertz-wave detection side is coupled to the waveguide of a terahertz-wave element 24 according to this embodiment described above. In this case, the terahertz-wave detection side may be spatially coupled to the light from the femtosecond laser 20 using a lens via an optical delay unit 29. Alternatively, a delay unit (not shown) using a fiber stretcher for achieving an all fiber configuration may be used, or an optical delay unit may be disposed at the terahertz-wave generation side. In that case, the detection side may be constituted by integrating a Selfoc lens with the fiber end or may be of a pigtail type formed by processing the aforementioned end so that the numerical aperture thereof is smaller than or equal to the numerical aperture of the waveguide of the Cerenkov phase-matching element. In this case, the ends may each be provided with a nonreflective coating so as to reduce Fresnel loss and undesired interference noise. Alternatively, by designing the fiber 23 and the waveguide so that they have similar numerical apertures and similar mode field diameters, direct coupling (butt-coupling) by abutment is also permissible. In this case, an adhesive is appropriately selected so that an adverse effect caused by reflection can be reduced.

If the fiber 22 or the femtosecond laser 20 at the preceding stage includes a non-polarization-maintaining fiber component, it is preferable to stabilize the polarization of input light entering the terahertz-wave element 24 according to the present invention by using an inline-type polarization controller.

However, the excitation light source is not limited to a fiber laser, and in that case, the countermeasure for stabilizing the polarization is reduced.

A terahertz wave is generated by, for example, irradiating light output from the optical fiber 22 onto a photoconductor 28, is made into a collimated beam by a parabolic mirror 26a, and is split by a beam splitter 25. One of the split beams is irradiated onto a sample 30 via a parabolic mirror 26b. The terahertz wave reflected from the sample 30 is collected by a parabolic mirror 26c and reaches the terahertz-wave element 24 and a detector 27. The photoconductor 28 used is normally a dipole antenna formed using low-temperature growth InGaAs if the center wavelength of the light source corresponds to 1.55 μm. As mentioned above, the detector 27 includes, for example, the Wollaston prism 9 and the two photodiodes 10 and 11.

Figure 4:
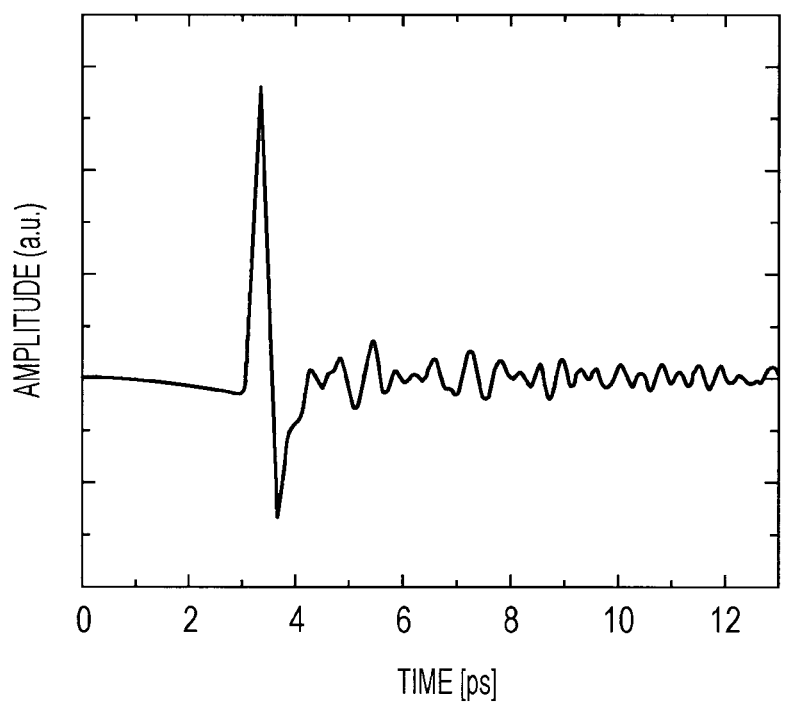
FIG. 4 illustrates an example of a terahertz waveform according to the first embodiment of the present invention.

The apparatus is configured to modulate voltage applied to the photoconductor 28 by a power source unit 31 and synchronously detect an output from the detector 27, which detects light whose propagating state has been changed by the terahertz-wave element 24, by using a signal acquiring unit 32 via an amplifier 34. A data processing and output unit 33 is configured to acquire a terahertz signal waveform while using a personal computer or the like to move the optical delay unit 29. FIG. 4 illustrates an example of a terahertz pulse waveform acquired only from surface reflection when the sample 30 is a mirror.

In this system, the reflected wave from the sample 30 to be measured and the irradiated terahertz wave are coaxial with each other, and the power of the terahertz wave is reduced by half. Therefore, the irradiated terahertz wave and the reflected wave may be made non-coaxial with each other by increasing the number of mirrors, as in FIG. 3B, so as to increase the power of the terahertz wave, although the incident angle on the sample 30 in this case becomes unequal to 90°.

If there is a discontinuous section in the material inside the sample 30, a signal to be acquired would have a reflective echo pulse occurring at a time position corresponding to the discontinuous section. Thus, a tomographic image can be obtained by one-dimensionally scanning the sample 30, or a three-dimensional image can be obtained by two-dimensionally scanning the sample 30.

With the tomography apparatus according to this embodiment, the internal penetration depth and the depth resolution can be improved. Furthermore, since an excitation laser using fibers can be used as an irradiating unit, the apparatus can be reduced in size and cost.

Although light is input from an end opposite to the generation side in this embodiment, light may alternatively be input from the same side as the generation side. In that case, the signal strength becomes smaller since the matching length is reduced.

Although the excitation light source used is of an ultrashort pulse type, the above embodiment can also be applied to a case where a single-wavelength terahertz wave based on differential frequency generation is to be detected with a continuous wave or a nanosecond-order pulse by using two lasers having different wavelengths.

Although an LN crystal is used as the material for the crystal, other alternative examples of electro-optic crystals include LiTaOx, NbTaOx, KTP, DAST, ZnTe, and GaSe, as mentioned in the background art.

Example 1

In the element structure shown in FIGS. 1A and 1B in this example, the optical adhesive layer 2 having a refractive index n of about 1.5 is formed with a thickness of 3 μm, the waveguide layer 4 composed of an MgO-doped LN crystal is formed with a thickness of 3.8 μm and a width of 5 μm, and the low-refractive-index buffer layer 5 composed of the same optical adhesive as that used for the optical adhesive layer 2 is formed with a thickness of 3 μm. A high-resistivity Si prism is used as the optical coupling member 7. Specifically, in order to satisfy Cerenkov phase-matching, a prism with an angle θ of 41° is attached so that a terahertz wave can orthogonally enter the prism surface at an angle θclad of 49°. Although the surfaces that are not the terahertz-wave input surface appears as if they are inclined, the angle of these surfaces is arbitrary, such as a right angle. Although the length of the waveguide is set to, for example, 10 mm, the length is not limited to this value.

The thickness of the waveguide layer 4 is determined as follows. Specifically, a maximum frequency fmax is determined from a Fourier frequency band to be detected as a terahertz pulse. Then, the thickness of the waveguide layer 4 is set such that the thickness is smaller than or equal to half the length of an equivalent wavelength within the crystal, corresponding to the maximum frequency fmax, and that a single mode condition corresponding to a good coupling efficiency and a low propagation loss of input ultra-short pulse laser light is satisfied. In order to handle up to, for example, 7.5 THz in this example, the wavelength in a free space is about 40 μm, and if the refractive index of the terahertz wave in the LN waveguide layer is 5.2, the thickness of the waveguide layer is preferably $\lambda_{eq}(THz)/2(=40/5.2/2)=3.8$ μl. On the other hand, in view of coupling efficiency and propagation loss, waveguide simulation results show that the optical waveguide in this example preferably has a thickness of about 5 μm if the center wavelength of the input laser light is 1.55 μm. However, the lower condition, that is, the thickness of 3.8 μm for the waveguide, is preferentially selected so as to ensure a terahertz wave band. In this case, fmax=7.5 THz in this example corresponds to a frequency of LO phonon absorption of the LN crystal and is set in view of the fact that the terahertz wave is significantly absorbed and not released near that frequency. There are cases where detection of, for example, 10 THz or higher, which is a frequency that is higher than the LO phonon absorption band, is possible depending on the pulse width of the input laser light. In that case, the thickness of the optical waveguide is reduced accordingly. Furthermore, if the center wavelength of the input laser light is 1 μm, an optimal thickness is about 3.6 μm based on simulation. In this case, this thickness is selected. It is thus important to determine the thickness of the waveguide layer 4 in view of the differences in the required terahertz band or the condition of a good coupling efficiency and a low propagation loss of input laser light, and it is preferable to select the lower one of these two conditions as an optimal mode.

On the other hand, the low-refractive-index buffer layer 5 with a thickness of 2 μm is formed using the same optical adhesive as that used for the optical adhesive layer 2. Similarly, in order to handle up to 7.5 THz, assuming that the equivalent wavelength is equal to a value divided by the refractive index 1.5 of the low-refractive-index buffer layer 5, the thickness is set to 2 μm, which is smaller than or equal to $\lambda_{eq}/10$ (=40/1.5/10)=2.7 μM, as mentioned in the first embodiment.

Second Embodiment

Figure 5A:
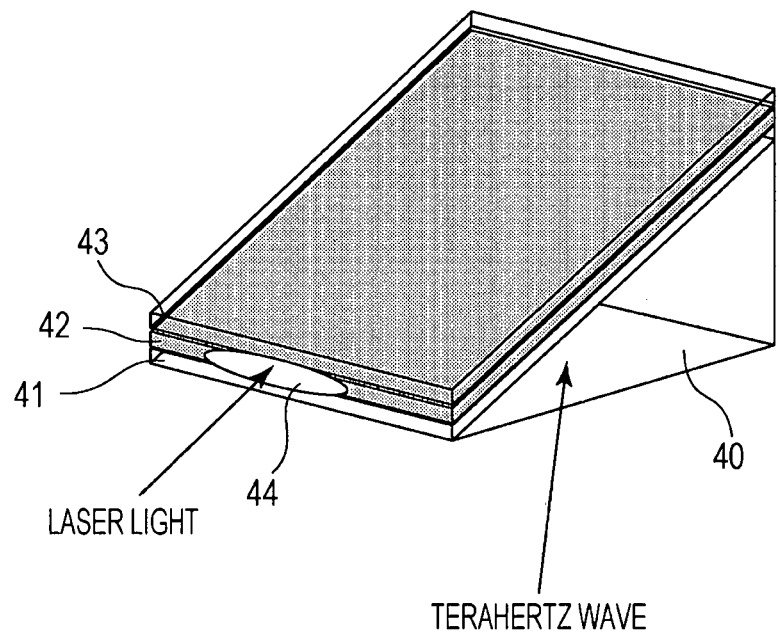
FIGS. 5A and 5B are structural diagrams of a terahertz-wave element according to a second embodiment of the present invention.
Figure 5B:
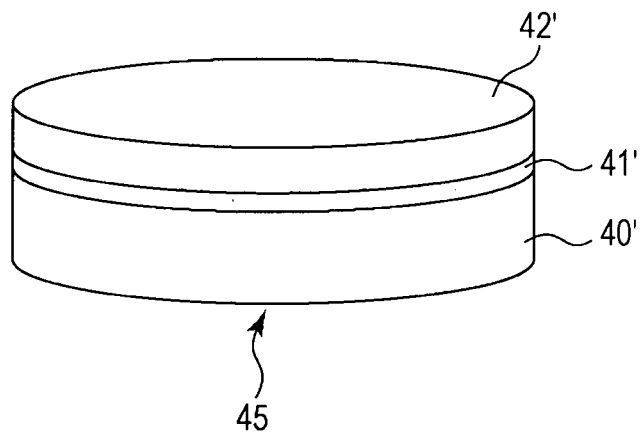

A second embodiment of the present invention will now be described with reference to FIGS. 5A and 5B. This embodiment uses a sandwich-type slab waveguide as a waveguide layer 42 through which laser light propagates, and does not have an LN substrate that holds the waveguide layer 42. The length of the waveguide is set to, for example, 5 mm. FIGS. 5A and 5B differ from FIGS. 1A and 1B in that the prism side is shown as the lower side.

The sandwich-type slab waveguide can be achieved by preparing a bonding wafer 45, as shown in FIG. 5B. The bonding wafer 45 is formed by adhering an MgO-doped LN crystal substrate 42', which is to become a waveguide, onto a high-resistivity Si substrate 40', which is a material to become a prism 40, by using an adhesive 41' (the same as that in the first embodiment), which is to become a low-refractive-index buffer layer. The LN crystal substrate 42' is ground until reaching the thickness of the waveguide. After the grinding, a low-refractive-index layer 43 made of resin or an oxide film, such as $SiO_2$, for protection is preferably formed on the waveguide layer 42 (FIG. 5A). Even if this low-refractive-index layer 43 is not to be provided, light can still be confined in the waveguide layer since the refractive index of air is low.

An Si prism may be given an inclined section by grinding or chemical etching. For example, in the case of a (100) Si substrate, known wet etching (such as KOH) may be performed so as to form a (111) surface with a 55° inclination angle. Although this surface deviates by 14° from an ideal surface having a 41° inclination angle, an increase in reflection loss (Fresnel loss) at the surface is minimal. It is needless to say that an inclined substrate may be used for achieving a 41° surface.

The input light may be in the shape of an oval, as denoted by reference numeral 44. In that case, a rod lens or a cylindrical lens may be used as a lens for coupling the light from the laser light source so that the light is throttled in the vertical direction of the layered structure of the waveguide.

Although a light detecting unit in the later stage is omitted, the terahertz-wave detecting method is the same as that in the first embodiment.

The use of the slab waveguide in this embodiment advantageously facilitates the coupling of probe light and allows for a wide interaction area even when the terahertz wave is insufficiently collected.

Third Embodiment

Figure 6:
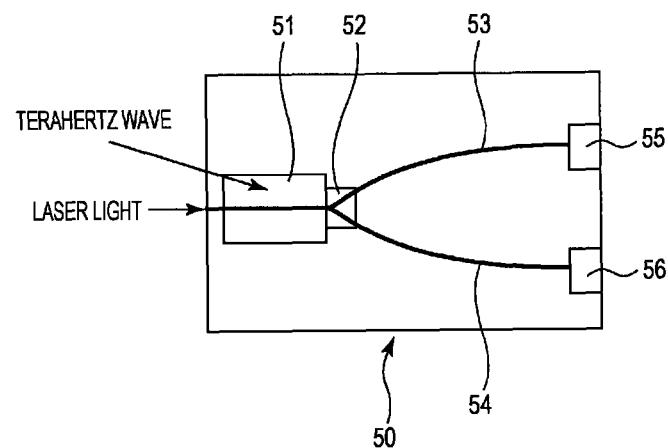
FIG. 6 is a structural diagram of a terahertz-wave element according to a third embodiment of the present invention.

In a third embodiment of the present invention, the detectors are also integrated on the same substrate, as shown in FIG. 6. A substrate 50 is provided with a terahertz-wave element 51 based on Cerenkov phase-matching, which is similar to that in the first embodiment. An output end of the terahertz-wave element 51 is provided with a waveguide-type polarizing beam splitter 52 that splits input light into two polarized components and guides the two polarized components to two integrated optical waveguides 53 and 54. Moreover, two light detectors 55 and 56 are integrated on the substrate 50 so as to detect light output from the waveguides 53 and 54. The outputs from the two light detectors 55 and 56 are used for detecting a terahertz-wave signal by balance reception, as in the first embodiment.

The waveguide-type polarizing beam splitter 52 can be achieved by forming a dielectric multilayer film at a Y-branch section of the waveguides 53 and 54. Furthermore, regarding the waveguides 53 and 54, the substrate 50 may be composed of Si, and Si waveguides may be fabricated by forming rectangular patterns on the Si substrate 50. If an excitation laser with a 1-μm band or lower is used, since the light is absorbed by Si, $SiO_2$ waveguides may be used. Regarding the light detectors 55 and 56, MSM detectors based on InGaAs may be integrated on the substrate 50.

In the case where the substrate 50 is composed of Si, as described above, the Si substrate may be etched as in the second embodiment so as to allow a terahertz wave to enter from the rear side (not shown) in the plan view of FIG. 6.

In this embodiment, the number of spatial coupling systems is reduced so that the element itself is made compact and stable, thereby advantageously reducing a loss of light when being guided to the light detectors 55 and 56. By using the element according to this embodiment as the terahertz-wave detecting element in the tomography apparatus described in the first embodiment, imaging performance can be enhanced.

Fourth Embodiment

Figure 7:
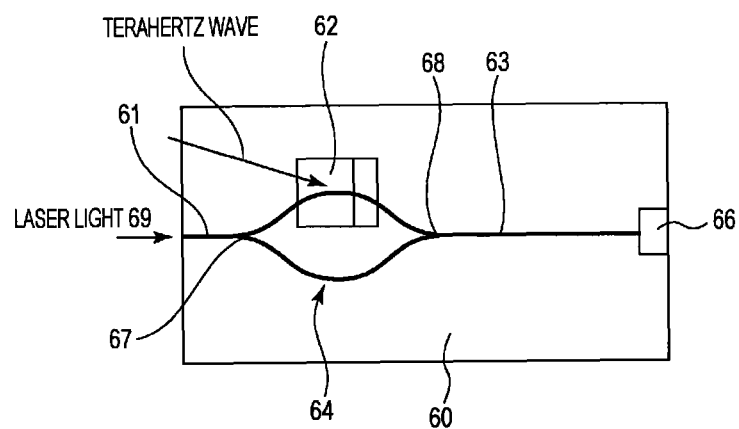
FIG. 7 is a structural diagram of a terahertz-wave element according to a fourth embodiment of the present invention.

As shown in FIG. 7 in plan view, a fourth embodiment according to the present invention provides an integrated element that includes a Mach-Zehnder interferometer 64 having a Y-branch section 67 and a coupler 68, and that causes an output from the Mach-Zehnder interferometer 64 to propagate through a waveguide 63 so as to acquire a signal using a light detector 66. The material used here can be a nonlinear optic crystal mainly composed of LN as in the above embodiments. The Y-branch section 67 branches a waveguide 61 into a detection waveguide (detection optical path) through which light to be detected propagates and a reference waveguide (reference optical path) through which reference light propagates. The waveguide in a terahertz-wave element 62 according to the present invention is included in the detection waveguide.

In this embodiment, a terahertz wave is detected by utilizing a change in the phase state of light instead of utilizing a polarization variation of light propagating through the waveguide.

Therefore, although the crystal-axis direction of the waveguide in the terahertz-wave element (Cerenkov phase-matching section) 62 is the same as that in the first embodiment, the polarization direction of input laser light 69 is set parallel to the Z axis. In that case, birefringence does not occur at the MgO-doped LN crystal layer, and a polarization variation does not occur even when the waveguides 61 and 63 are formed of this crystal.

When a terahertz wave enters as an S-polarized wave, the propagation velocity of propagating light changes since the refractive index changes due to the Pockels effect. Due to the Mach-Zehnder interferometer configuration, a phase difference occurs between the detection optical path and the reference optical path at the coupler 68 when the propagation velocity in one of the waveguides changes, causing a change in the light intensity due to interference.

Because this phase difference changes in accordance with the intensity of an input terahertz wave, a terahertz signal can be received by the light detector 66.

Since a polarization controller is not used in this embodiment, the structure is simplified. By using the element according to this embodiment as the terahertz-wave detecting element in the tomography apparatus described in the first embodiment, a compact and stable system can be achieved.

Fifth Embodiment

A fifth embodiment according to the present invention utilizes terahertz-wave generation using electro-optic Cerenkov radiation described in the first embodiment and provides a structure integrated with the terahertz-wave detecting element based on Cerenkov phase-matching according to the present invention.

Figure 8A:
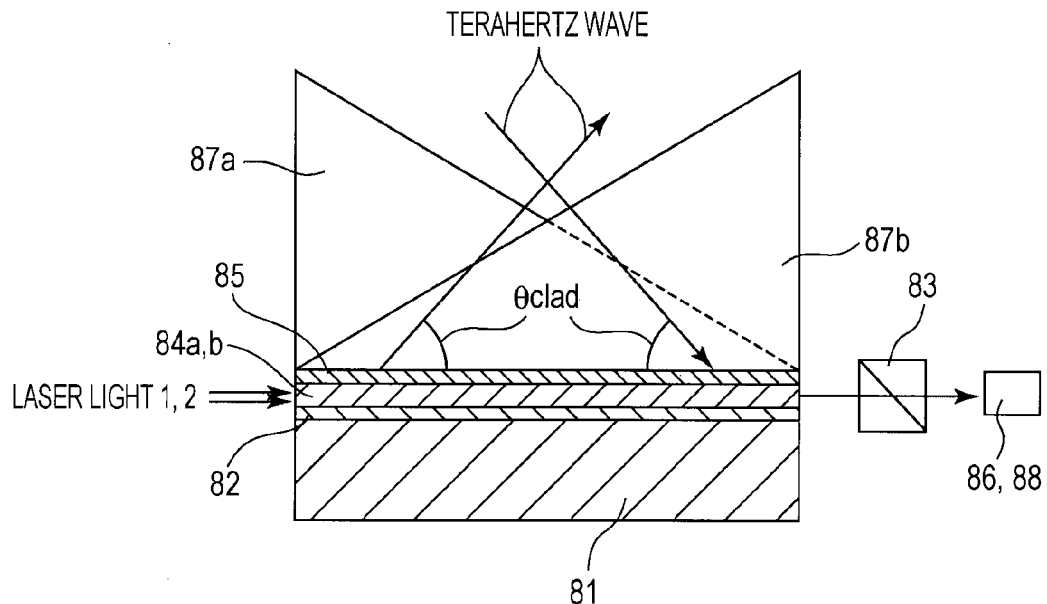
FIGS. 8A and 8B are structural diagrams of a terahertz-wave element according to a fifth embodiment of the present invention.
Figure 8B:
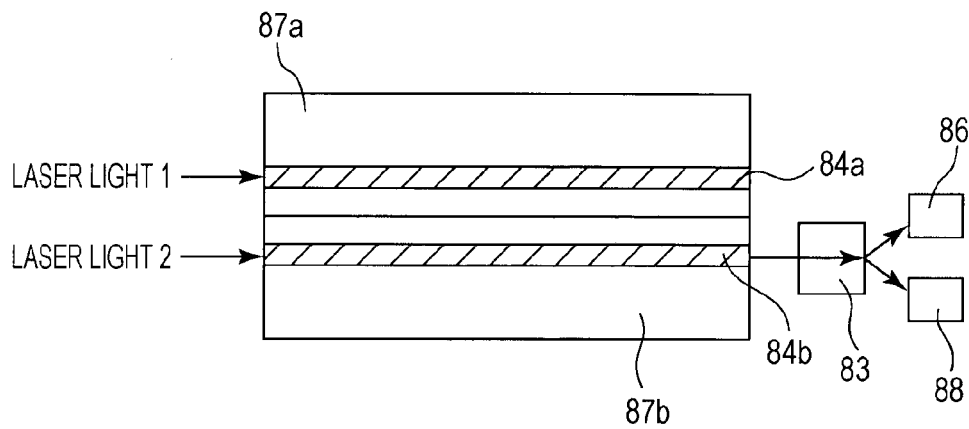

An example of the structure is illustrated in a cross-sectional view in FIG. 8A and a plan view in FIG. 8B. FIG. 8A is a cross-sectional view of a waveguide section through which laser light propagates. As shown in FIG. 8B in plan view, two waveguides 84a and 84b each formed of an MgO-doped LN crystal similar to that used in the first embodiment are provided parallel to each other in a single element. Reference numerals 81, 82, and 85 denote an LN substrate and upper and lower low-refractive-index adhesive layers, respectively, as in the first embodiment. Reference numeral 87 denotes an Si prism. As shown in FIGS. 8A and 8B, one of the waveguides (in this case, the waveguide 84a) corresponds to a known Cerenkov terahertz-wave generating element from which a terahertz wave is released to the space at an angle θclad of 49° due to laser light propagation. The other waveguide corresponds to a terahertz-wave detecting element according to the present invention and is configured to couple a terahertz wave to the waveguide 84b at an angle θclad of 49° via an Si prism 87b. Therefore, the waveguide 84a and the waveguide 84b are respectively provided with Si prisms (i.e., a first coupling member 87a and a second coupling member 87b) that are different from each other (specifically, inclined in different directions from each other). The inclination angles may be the same as in the first embodiment, and in that case, crosstalk between a generated terahertz wave and a detected terahertz wave is small. Probe light is input as second laser light to the waveguide 84b at the detection side, and input polarized light is tilted at 45° as in the first embodiment. A polarization splitter 83, such as a Wollaston prism, and two light detectors 86 and 88 are disposed at the output end so that the propagation state of the laser light changed due to the terahertz-wave signal can be acquired. Although the two waveguides 84a and 84b each have a width of 5 μm and are spaced apart from each other by about 1 mm, the waveguides 84a and 84b are not limited to this configuration. The waveguides 84a and 84b may alternatively be a slab waveguide having a generation section and a detection section that are separated from each other at a laser-light input position.

Figure 9:
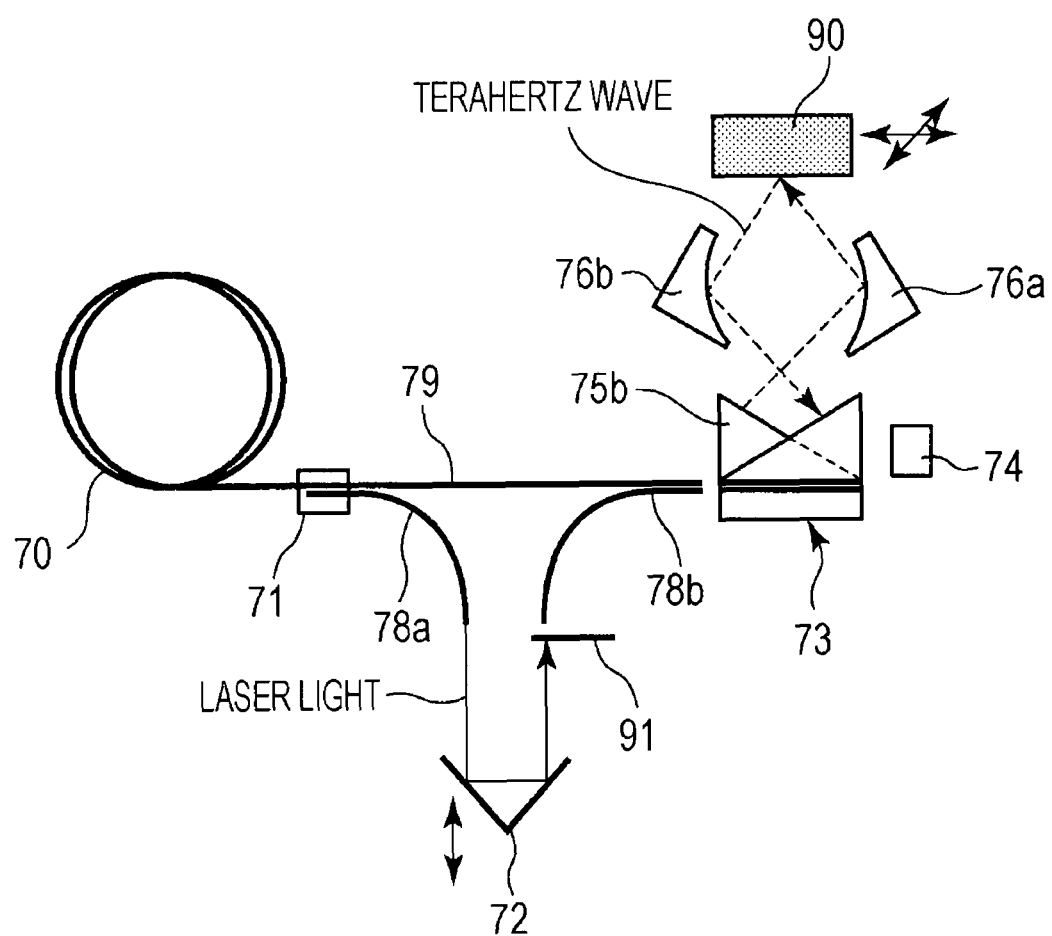
FIG. 9 is a configuration diagram of a tomography apparatus according to the fifth embodiment of the present invention.

An example of a terahertz time-domain spectroscopy system using such an integrated Cerenkov phase-matching element is illustrated in FIG. 9. An output from a fiber laser 70 is split into two components via a coupler 71, and one of the split components is guided as pump light (first laser light in FIGS. 8A and 8B) to an integrated Cerenkov phase-matching element 73 according to this embodiment via an optical fiber 79. The other split laser-light component is coupled to an optical fiber 78b from an optical fiber 78a via a delay optical unit 72 and a light chopper 91 and is guided as probe light (second laser light in FIGS. 8A and 8B) for the integrated Cerenkov phase-matching element 73. A generated terahertz wave is collected by a parabolic mirror 76a and is irradiated onto a sample 90. The terahertz wave reflected at the sample 90 is collected by a parabolic mirror 76b and is detected by the element 73 and a detector 74. The detector 74 includes the polarization splitter 83 and the two light detectors 86 and 88 shown in FIGS. 8A and 8B.

A tomographic-image acquiring method and a spectroscopy-information acquiring method using this system can be achieved by using known methods.

The fifth embodiment can provide an element in which a generator and a detector are integrated into a single unit, thereby providing a compact terahertz time-domain spectroscopy system.

Sixth Embodiment

Figure 10A:
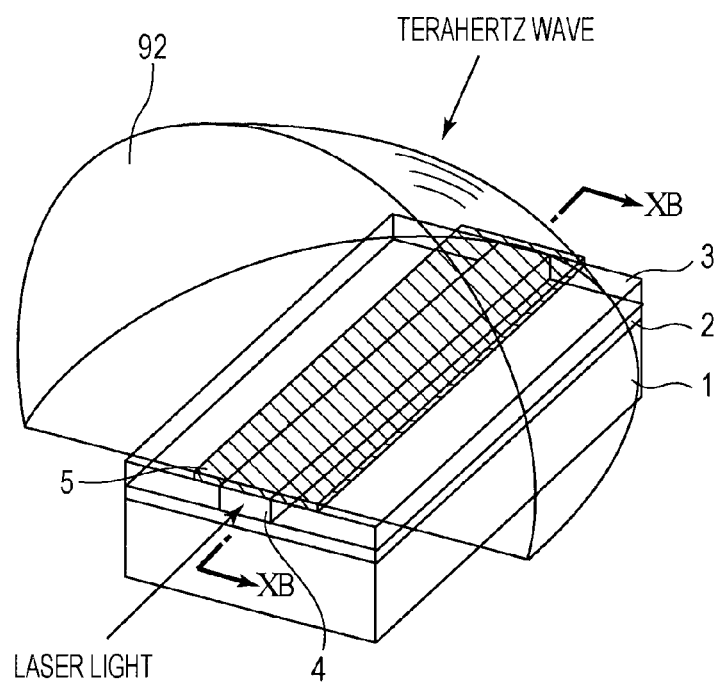
FIGS. 10A and 10B are structural diagrams of a terahertz-wave element according to a sixth embodiment of the present invention.
Figure 10B:
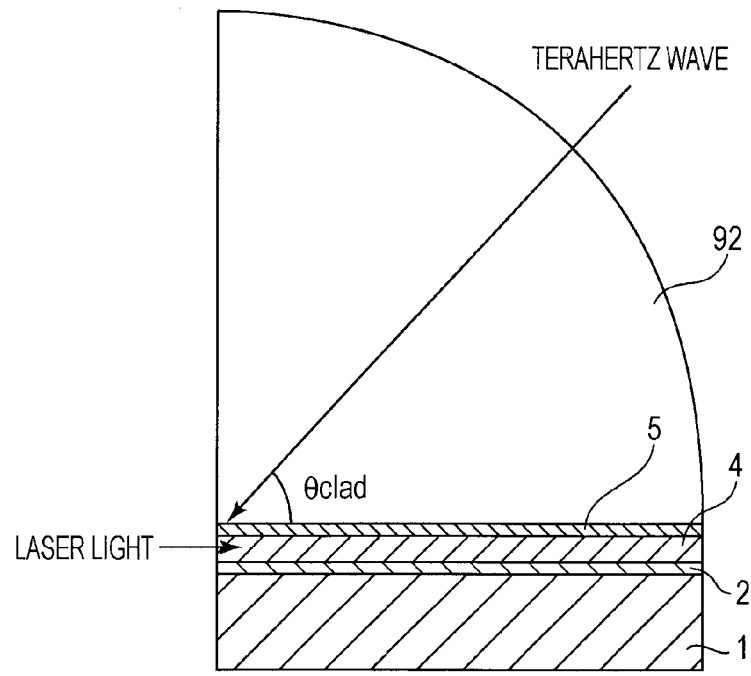

A sixth embodiment of the present invention relates to a configuration in which a coupling member is given a curved surface to enhance collectability of a terahertz wave. FIGS. 10A and 10B illustrate a structural body 92, serving as a coupling member, formed by cutting two faces of a hyper-hemispherical lens. In FIGS. 10A and 10B, components similar to those in FIGS. 1A and 1B are given the same reference numerals. In this case, since a terahertz wave is collected at a focal point of the lens, the terahertz wave is input from a direction different from that in the first embodiment. Specifically, the laser light and the terahertz wave are input from opposite directions. If an ultra-short pulse with several tens of fs or shorter is used as the laser light, since the pulse width expands within the waveguide due to wavelength dispersion, there are cases where a wideband can be achieved better by causing an interaction to occur near the input end.

Therefore, the terahertz wave is input at an angle θclad (49° if an Si member is used), as shown in FIG. 10B, and the focal point at the leading end of the arrow is set at, for example, a position that is 500 μm inward from an end of the waveguide.

By giving the waveguide a circular-arc-like curve in a cross section taken in a direction orthogonal to the propagating direction of the laser light, a terahertz wave from the lateral direction of the waveguide can also be collected, thereby increasing the utilization efficiency of the terahertz wave, as compared with when a triangular prism is used as in the first embodiment. Alternatively, the laser light and the terahertz wave may be input from the same direction (as in the first embodiment) by inverting the orientation of the lens.

Figure 11:
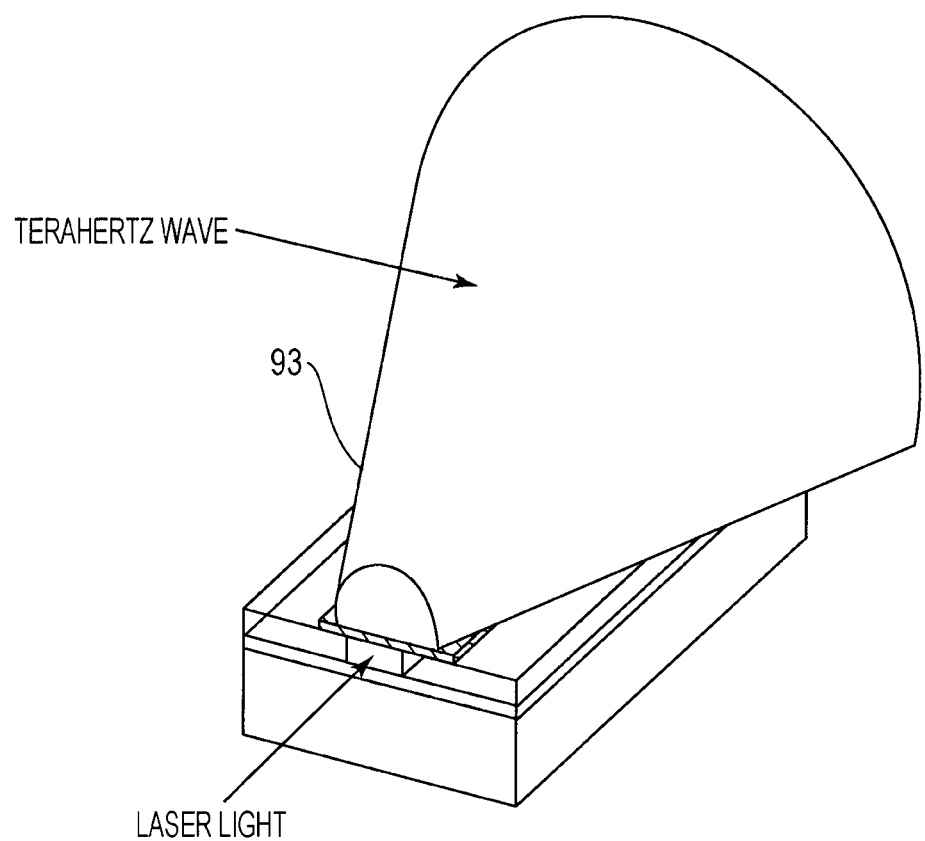
FIG. 11 is a structural diagram of another terahertz-wave element according to the sixth embodiment of the present invention.

As another structure in which the waveguide is given a circular-arc-like curve in a cross section taken in a direction orthogonal to the propagating direction of the laser light, a structural body 93 formed by cutting one face of a cone is also permissible, as shown in FIG. 11. In this case, a terahertz wave can be collected linearly without a focal point in the direction of the waveguide while also collecting a terahertz wave from the lateral direction of the waveguide. Therefore, the laser light and the terahertz wave can be input from the same direction as in the first embodiment, thereby allowing for an increased interaction distance. Consequently, the S/N ratio can be further improved, as compared with the case where a cut hyper-hemispherical lens is used as described above. The structural body 92 or the structural body 93 may be selected on the basis of the relationship between the S/N ratio and the band of a signal to be detected.

Although the waveguide and the coupling member are illustrated in FIGS. 10A to 11 as if their lengths match, the lengths do not necessarily need to match.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-006123 filed Jan. 14, 2011 and No. 2011-230004 filed Oct. 19, 2011, which are hereby incorporated by reference herein in their entirety.

REFERENCE SIGNS LIST 1 substrate
2 adhesive layer
3 waveguide surrounding region
4 waveguide layer
5 low-refractive-index buffer layer
7 optical coupling member

The invention claimed is:

1. A terahertz-wave element comprising:
a waveguide that includes an electro-optic crystal and allows light to propagate therethrough; and
a coupling member that causes a terahertz wave to enter the waveguide,
wherein a propagation state of the light propagating through the waveguide changes as the terahertz wave enters the waveguide via the coupling member,
wherein the waveguide includes a core layer and a cladding layer,
wherein the cladding layer is interposed between the coupling member and the core layer, and
wherein $a<d<\lambda_{eq}/10$ is satisfied where d denotes a thickness of the cladding layer, a denotes a thickness corresponding to $1/e^2$ of a light intensity of the light in the core layer, e being the base of natural logarithm and $\lambda_{eq}$ denotes an equivalent wavelength in the cladding layer with respect to a wavelength corresponding to a maximum frequency of the terahertz wave.

2. The terahertz-wave element according to claim 1, wherein the waveguide includes a core layer and a cladding layer, and
wherein a thickness of the core layer is smaller than or equal to half a length of an equivalent wavelength in the core layer, corresponding to a maximum frequency of the terahertz wave.

3. The terahertz-wave element according to claim 1, wherein an angle $\theta_c$ formed between the light and the terahertz wave satisfies the following equation:

$$\cos\theta_c = \frac{n_g}{n_{THz}}$$

where $n_g$ denotes an effective group refractive index of the light, and $n_{THz}$ denotes an effective refractive index of the terahertz wave.

4. A terahertz-wave detecting device comprising:
the terahertz-wave element according to claim 1; and
a detecting unit configured to detect the light propagating through the waveguide of the terahertz-wave element.

5. The terahertz-wave detecting device according to claim 4, wherein the detecting unit detects a polarization state of the light.

6. The terahertz-wave detecting device according to claim 5, wherein the electro-optic crystal includes Y-cut lithium niobate,
wherein if a propagating direction of the light in the waveguide is defined as an X axis and a direction orthogonal to the propagating direction is defined as a Z axis, the light input to the waveguide is polarized light including a Y-axis component and a Z-axis component of an electric field, and
wherein the detecting unit includes a polarization splitter that splits the light propagating through the waveguide into linearly-polarized light components polarized in different directions, and a light detector that detects the linearly-polarized light components.

7. The terahertz-wave detecting device according to claim 6, wherein the polarization splitter, the light detector, and the waveguide are formed on a single substrate, and wherein the polarization splitter and the light detector are coupled to each other by the waveguide.

8. The terahertz-wave detecting device according to claim 5, wherein the detecting unit detects a phase state of the light.

9. A terahertz time-domain spectroscopy system comprising the terahertz-wave detecting device according to claim 4.

10. A tomography apparatus comprising the terahertz time-domain spectroscopy system according to claim 9.

11. The terahertz-wave element according to claim 1, wherein, in a cross section taken in a direction orthogonal to a propagating direction of the light in the waveguide, the coupling member has a curve in a portion thereof other than a surface thereof that is in contact with the electro-optic crystal.

12. A terahertz-wave element comprising:
a first waveguide including an electro-optic crystal;
a second waveguide including an electro-optic crystal;
a first coupling member that extracts a terahertz wave, which is generated from the electro-optic crystal due to light propagating through the first waveguide, to a space; and
a second coupling member that causes the terahertz wave to enter the second waveguide from the space.

13. A terahertz-wave detecting device comprising:
i) a terahertz-wave element including:
a waveguide that includes an electro-optic crystal and allows light to propagate therethrough; and
a coupling member that causes a terahertz wave to enter the waveguide,
wherein the waveguide includes a core layer, and
wherein a thickness of the core layer is smaller than or equal to half a length of an equivalent wavelength in the core layer, corresponding to a maximum frequency of the terahertz wave; and
ii) a detecting unit configured to detect the light propagating through the waveguide of the terahertz-wave element.

14. The terahertz-wave detecting device according to claim 13, wherein the detecting unit detects a polarization of the light.

15. The terahertz-wave detecting device according to claim 13, wherein the detecting unit detects a phase state of the light.

16. A terahertz-wave element comprising:
a waveguide that includes an electro-optic crystal and allows light to propagate therethrough; and
a coupling member that causes a terahertz wave to enter the waveguide,
wherein a propagation state of the light propagating through the waveguide changes as the terahertz wave enters the waveguide via the coupling member,
wherein the waveguide includes a core layer,
wherein a thickness of the core layer is smaller than or equal to half a length of an equivalent wavelength in the core layer, corresponding to a maximum frequency of the terahertz wave.

* * * * *